United States Patent [19]

Berger et al.

[11] 4,049,967
[45] Sept. 20, 1977

[54] X-RAY EXAMINING APPARATUS INCLUDING A TOMOGRAPHIC EXPOSURE INSTALLATION

[75] Inventors: Helmut Berger; Gunther Holzermer; Harry Kirsch, all of Erlangen, Germany; Pieter Vijlbrief, Leiden, Netherlands

[73] Assignee: Siemens Aktiengesellschaft, Berlin & Munich, Germany

[21] Appl. No.: 604,079

[22] Filed: Aug. 12, 1975

[30] Foreign Application Priority Data

Aug. 21, 1974  Germany .............................. 2440146

[51] Int. Cl.² .......................................... G01N 21/34
[52] U.S. Cl. ................................. 250/445 T; 250/476
[58] Field of Search ............................ 250/476, 445 T

[56] References Cited

U.S. PATENT DOCUMENTS

| | | |
|---|---|---|
| 2,936,370 | 5/1960 | Green et al. .......................... 250/476 |
| 3,263,647 | 8/1966 | Murphy et al. .................. 250/476 X |
| 3,714,428 | 1/1973 | Gasaway ......................... 250/476 X |
| 3,818,220 | 6/1974 | Richards ..................... 250/445 T X |

Primary Examiner—Davis L. Willis
Attorney, Agent, or Firm—Hill, Gross, Simpson, Van Santen, Steadman, Chiara & Simpson

[57] ABSTRACT

An X-ray examining apparatus including a tomographic exposure installation, with an adjusting or positioning drive for the laminagraphic height displacement, as well as an installation for effecting the marking or indentifying of the currently set laminagraphic height on the tomographic X-ray exposures. In an X-ray examining apparatus of the above-mentioned type there is, accordingly, inventively associated with the X-ray film sheets which are being exposed, a scale or graduated dial which is provided with laminagraphic height gradations and coupled with the positioning drive for the laminagraphic height for the imaging of the area identifying the currently set laminagraphic height.

5 Claims, 9 Drawing Figures

0°  90° 180° 270° 360°

X-RAY EXAMINING APPARATUS INCLUDING A TOMOGRAPHIC EXPOSURE INSTALLATION

FIELD OF THE INVENTION

The present invention relates to an X-ray examining apparatus including a tomographic exposure installation, with an adjusting or positioning drive for the laminagraphic height displacement, as well as an installation for effecting the marking or identifying of the currently set laminagraphic height on the tomographic X-ray exposures.

DISCUSSION OF THE PRIOR ART

In the publications "Roentgenblattern" (XIII year, Volume 4, April 1960; page 98, FIG. 1, line 7, through page 100, line 5) an article has appeared in which a report has been made with reference to a leader having a sprocket spacing of 4 mm and which is located in the X-ray path at an incline to the exposure plane, by means of which the laminagraphic elevation can be marked on the tomographic X-ray exposures. The sprockets which are presently at precisely the elevation of the set laminagraphic plane are sharply imaged on the X-ray film during the tomographic X-ray exposure. They provide for information with respect to the elevational position of the X-rayed layer in the body of a patient. However, in this extremely simple installation, it has been found as being disadvantageous that, on the film sheets, there must be maintained free a relatively large border area which encompasses the entire length of the leader for the projection of the sprocket which corresponds to the current laminagraphic height. This border area is lost to the actual X-ray exposures.

SUMMARY OF THE INVENTION

Accordingly, it is an object of the present invention to develop an installation of the above-mentioned type which facilitates the marking or identification of the set laminagraphic height on the tomographic X-ray exposures, and which requires therefore the smallest possible space on the film sheets. In an X-ray examining apparatus of the above-mentioned type there is, accordingly, inventively associated with the X-ray film sheets which are being exposed, a scale or graduated dial which is provided with laminagraphic height gradations and coupled with the positioning drive for the laminagraphic height for the imaging of the area identifying the currently set laminagraphic height. The foregoing will assure that, for the identification of the currently set laminagraphic height, only an extremely small area is presently required at the same location on the X-ray film sheet. This will produce an improved utilization of the film material.

A simplification of the X-ray examining apparatus can be attained by means of an advantageous further feature of the invention when the laminagraphic height gradations on the scale dial are adapted to be imaged by means of X-rays, and the scale dial including the area identifying the current laminagraphic height in immediate adjacency to the film-proximate ray dispersion, are supported so as to project into the focused X-ray beam cone. As a result of this further feature, any additional optical picture transmission means become superfluous and, moreover, the laminagraphic height is imaged on the X-ray film in synchronism with the tomographic X-ray exposure.

A particularly advantageous construction of the X-ray examining apparatus is achieved when the scale dial, in a suitable configuration of the invention, is adjustably supported on a base plate which incorporates a slide member which, at the current intersecting location of two diaphragm plates, is concurrently longitudinally displaceably guided on both diaphragm plates. In that manner, the indications of the laminagraphic heights, independently of the selected focusing and the selected film format, always appear in the same corner of the tomographic X-ray exposures. Connected thereby is the further advantage that the indications for the laminagraphic height are located in an area of the tomographic X-ray exposures which, in general, is of no significance to the diagnostic position.

BRIEF DESCRIPTION OF THE DRAWINGS

Further advantages of the invention may now be ascertained from the following detailed description thereof, taken in conjunction with the accompanying drawings; in which.

DETAILED DESCRIPTION

Figure 1:
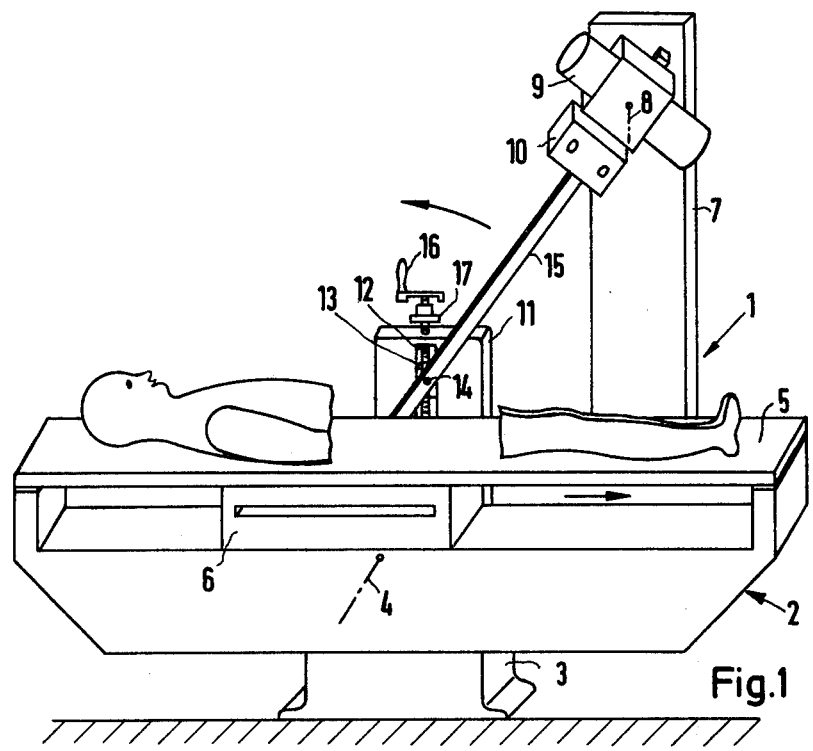
FIG. 1 is a perspective side elevational view of the X-ray examining apparatus pursuant to the invention.

FIG. 1 illustrates an X-ray examining apparatus 1 which includes a horizontally positioned examination table 2. The examination table is supported on a pedestal 3 so as to be tiltable about a horizontal axis 4, and is provided with a longitudinally displaceable patient's support plate or pallette 5. Built into the examination table 2, immediately below the patient's support pallette 5, is an exposure installation 6 which is adjustable along the longitudinal direction of the table. Longitudinally moveable, through a motor drive, at the side of the examination table there is provided on the examination table a tube turret 7 having an X-ray tube 9 rotatable about a horizontal axis 8 extending transverse of the longitudinal axis of the table with a flange-mounted depth focus 10. In addition, the pedestal 3 also supports a planigraphic stand 11. Located within the planigraphic stand is a vertical spindle 12 with a spindle nut 13. The spindle nut supports a pendulum axle 14 oriented in parallel to the axis 8 about which the X-ray tube 9 is rotatably supported on the tube turret 7. Pivotally supported on the pendulum axle 14 is a pendulum rod 15 which is coupled with the X-ray tube 9. Recognizable above the planigraphic stand in FIG. 1 is a hand-wheel 16 by means of which there may be rotated the spindle 12. Mounted on the planigraphic stand is further a rotational angle indicator 17 which is coupled with the spindle.

Figure 2:
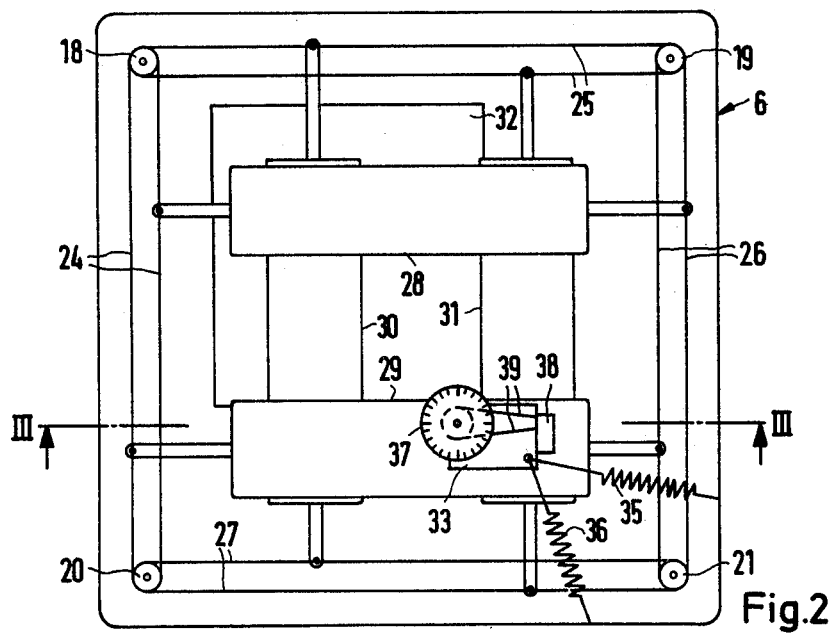
FIG. 2 is a sectional plan view of the exposure installation taken immediately above the plane of the film-proximate X-ray dispersion.
Figure 3:
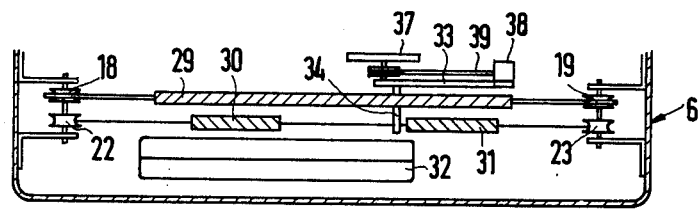
FIG. 3 is a sectional view taken along line III—III in FIG. 2.

In FIG. 2, which shows a plan view of exposure installation 6 sectioned in parallel to the plane of the patient's support pallette 5, there may be ascertained cable lines 24, 25, 26 and 27, which are conducted over rollers 18, 19, 20, 21, 22 and 23, for effectuating the mutually opposite displacement of the film-proximate diaphragm plates 28, 29, 30, 31. An X-ray film cassette 32 which is partially covered by the diaphragm plates is supported eccentrically of the focused X-ray field for the production of divided exposures. Located on the lower diaphragm plate 29 represented in the embodiment of FIG. 2 is a base plate 33 which is provided for with a finger-shaped slide member 34 extending perpendicular to the film plane, as may be ascertained in FIG. 3, which is pressed by two tension springs 35, 36 anchored in a housing wall of the exposure installation, in the right-hand lower corner of the focused X-ray field, as shown in FIG. 2, against the there at right-angle intersecting diaphragm plates 29, 31. FIGS. 2 and 3 illustrate the arrangement of a scale dial 37 and a step motor 38 associated with the scale dial, which are located on the plate 33. In FIG. 2 there may also be recognized a toothed-belt drive 39, by means of which the step motor 38 is adapted to rotate the scale dial. The drive of the dial may also be constitued of a Bowden cable arrangement. (A Bowden cable is defined in Webster's Third New International Dictionary of the English Language Unabridged, 1965, as: "spring steel wire enclosed in a spiral wire casing for transmitting longitudinal motion at a distance esp. (as in a hand brake) around curves.") A stray radiation scanner, which is located between the diaphragm plates and the X-ray film cassette, together with its drive, is omitted for purposes of clarity.

Figure 4:
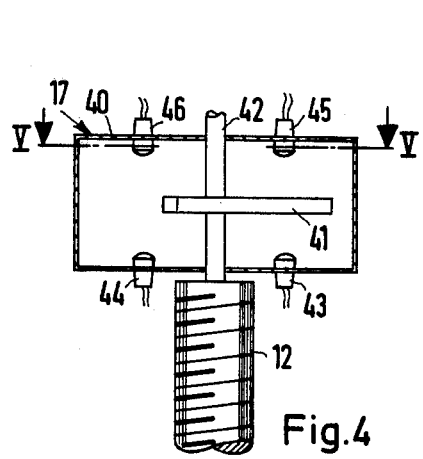
FIG. 4 is a vertical sectional view taken through the rotational angle indicator for the laminagraphic elevation.
Figure 5:
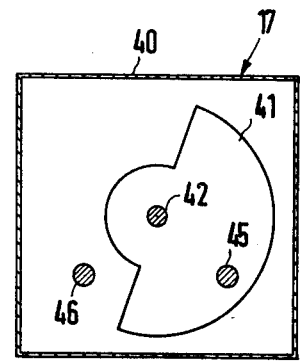
FIG. 5 is a sectional view taken along line V—V in FIG. 4.

FIGS. 4 and 5 illustrate, in section, a rotational angle indicator 17 which is fastened on the laminagraphic stand 11, and which is coupled with the spindle 12. Recognizable in the housing 40 of the rotational angle indicator is also an approximately semicircularly-shaped cutout disc 41 which is mounted on the axis of 42 of the spindle 12. In the area of the circumference of this semicircularly-shaped cutout disc there are located two light sources 43, 44 on one side in the housing of the rotational angle indicator and, on the other side, two photocells 45, 46 positioned each respectively opposite one of the two oppositely located light sources, so that the light beam is interrupted through the not cutout portion of the semicircularly-shaped disc 41. The two light sources 43, 44, and therewith the oppositely located photocells 45, 46, are offset with regard to each other by 90°, having reference to the axis 42 of the spindle 12 and the semicircularly-shaped disc 41.

Figure 6:
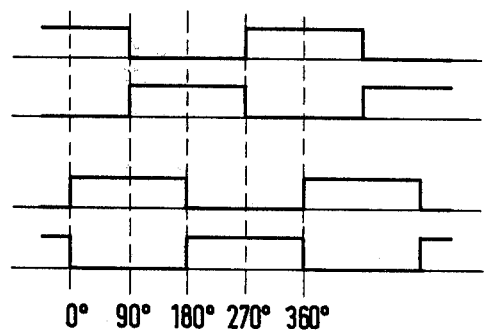
FIG. 6 is a graphical representation of the switching signals provided for by the rotational angle indicator during the course of a full rotation of the spindle.

Prior to the setting of a tomographic X-ray exposure, the desired laminagraphic elevation is set through rotational of the spindle 12 by means of the handwheel 16. Hereby, not only is the spindle nut 13 with the pendulum axle 14 displaced in height but, concurrently, semicircularly cutout disc 41 which is fastened on the spindle axis is rotated with the rotational angle indicator 17. This circularly-shaped cutout disc, during the course of a rotational of 360°, interrupts the two light streams to the two photocells 45, 46, in the manner illustrated in FIG. 6, once each and again sets these free for one time. The timewise sequence for the control of the photocells as indicated in FIG. 6, is also singularly meaningful in its indication with respect to the direction of rotation.

Figure 7:
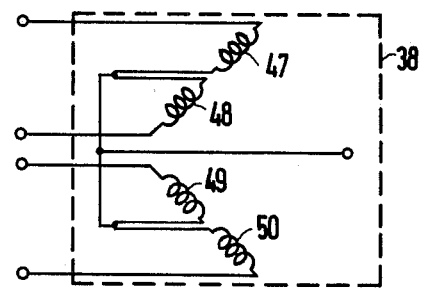
FIG. 7 is a circuit arrangement of a step-motor for effecting the laminagraphic height displacement.
Figure 8:
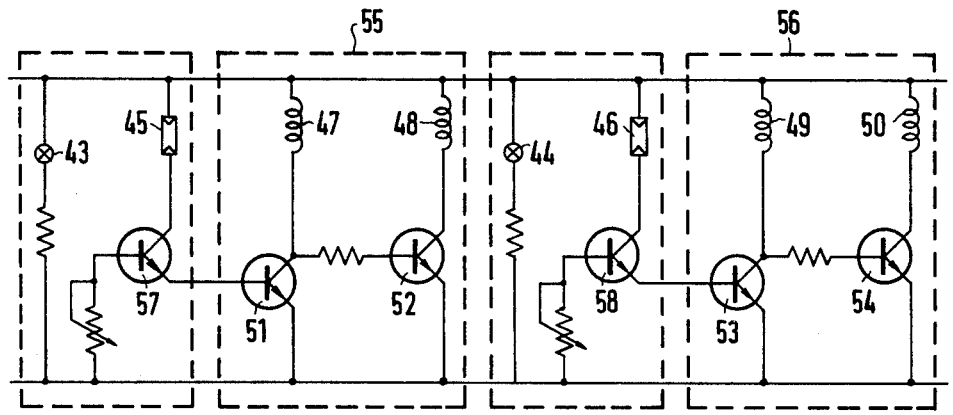
FIG. 8 is a circuit arrangement for the control of the step-motor through the intermediary of photocells.

FIG. 7 illustrates the circuit arrangement for the four windings 47, 48, 49, 50 of the step motor 38. From the circuit illustrated in FIG. 8 there may be recognized that each of the four windings are connected in series with the collector-emitter section of, respectively, a transistor 51, 52, 53, 54 of each of a flip-flop circuit 55, 56, which are both controlled through the emitter of a transistor 57, 58 each connected in series to respectively one of the photocells 45, 46. Due to the digital association of the individual switching impulses to a rotational angle of currently 90°, even at continued displacement no rotational angle errors creep in between the spindle 12 and the scale dial 41. By means of a further step motor connected in parallel to the previously mentioned step motor, there may be also driven an auxiliary indicator arrangement for the laminagraphic elevation at the operating or control console of the X-ray examining apparatus. In order to prevent a planigraphic height displacement at a switched-off current supply, an arresting arrangement is provided for the spindle which will only release the spindle at a switched-in current supply. Such an additional arresting arrangement may be omitted when the spindle, in a variation of the embodiment of FIG. 1, is only electronically displaceable or when, an electronic transducer is displaced in lieu of the disc 41, which has a servo-control for the scale dial associated therewith.

Figure 9:
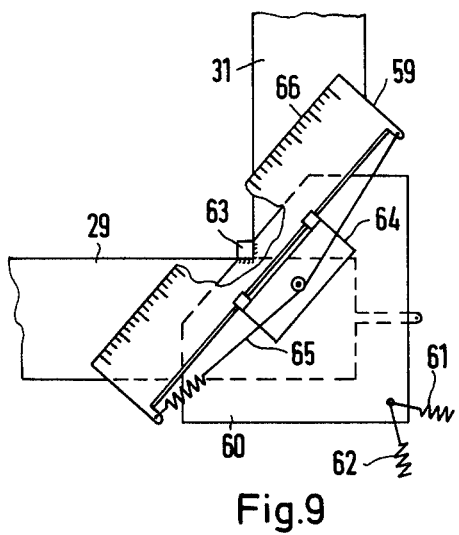
FIG. 9 is a modified type of arrangement of the scale dial at the film-proximate X-ray dispersion.

Finally, FIG. 9 illustrates another embodiment of the scale dial 59 with planigraphic elevation gradations. Similar to the embodiment of FIGS. 2 and 3, the base plate 60 is pressed by means of two springs 61, 62, together with its slide member 63, into one corner of the focused X-ray field against the two film-proximate diaphragm plates 29, 31. The scale dial is constructed in the form of a linear scale and is supported on the plate 60 so as to be longitudinally displaceable through step motor 64 by means of a cord drive 65. Hereby, the longitudinal axis of the scale disc is directed perpendicular to the angle bisect between the two diaphragm plates 29, 31 which lie against the base plate. The scale plate, with its forward edge 66 which carries the laminagraphic elevation gradations, projects its corner into the focused X-ray field, and namely so, whereby only the laminagraphic elevation gradations corresponding to the currently set laminagraphic plane appear in the X-ray field.

While there has been shown what is considered to be the preferred embodiment of the invention, it will be obvious that modifications may be made which come within the scope of the disclosure of the specification.

What is claimed is:

1. In an X-ray examining apparatus including a tomographic X-ray exposure installation; positioning drive means for effecting laminagraphic height adjustment; and means for making the presently set laminagraphic height on the tomographic X-ray exposures, the improvement comprising: scale dial means having laminagraphic height gradations thereon being operatively connected to said positioning drive means and associated with X-ray film sheets during exposure of the latter so as to mark the area representative of the currently set laminagraphic height on said film sheets; a position indicator connecting said scale dial means with the positioning drive means, said position indicator comprising an elongated casing with a relatively longitudinally displaceable wire therein, connecting said scale dial means with the positioning drive means for the laminagraphic height adjustment; said laminagraphic height gradations on said scale dial means being reproducible through X-rays; and means for supporting the scale dial means and the area representative of the currently set laminagrahic height in adjacency to film-proximate diaphragm means so as to project into the cone of the focused X-rays; said diaphragm means including at least two diaphragm plates; a base plate adjustably supporting said scale dial means, said base plate including a slide member supported on said diaphragm plates for concurrent longitudinal movement along the intersecting location of said two diaphragm plates; said scale dial means comprising a circular scale plate; means for rotatably supporting said scale plate, said scale plate having the laminagrahic gradations on the circumferential edge zones thereof extending above the edges of said diaphragm means defining the X-ray cone and projecting into said X-ray cone.

2. In an X-ray examining apparatus including a tomographic X-ray exposure installation; positioning drive means for effecting laminagraphic height adjustment; and means for marking the presently set laminagraphic height on the tomographic X-ray exposures, the improvement comprising: scale dial means having laminagraphic height gradations thereon being operatively connected to said positioning drive means and associated with X-ray film sheets during exposure of the latter so as to mark the area representative of the currently set laminagraphic height on said film sheets; a step motor connected to said scale dial means; and rotational angle indicator being connected to said positioning drive means for laminagraphic height adjustment controlling said step motor.

3. An X-ray examining apparatus as claimed in claim 2, said laminagraphic height gradations on said scale dial means being reproducible through X-rays; and means for supporting the scale dial means and the area representative of the currently set laminagraphic height in adjacency to film-proximate diaphragm means so as to project into the cone of the focused X-rays; said diaphragm means including at least two diaphragm plates; a base plate adjustably supporting said scale dial means, said base plate including a slide member supported on said diaphragm plates for concurrent longitudinal movement along the intersecting location of said two diaphragm plates; said scale dial means comprising a linear scale plate being displaceably supported so as to diagonally project relative to a corner of the focused X-ray cone into the X-ray cone in the longitudinal direction of the linear scale.

4. In an X-ray examining apparatus including a tomographic X-ray exposure installation; positioning drive means for effecting laminagraphic height adjustment; and means for marking the presently set laminagraphic height on the tomographic X-ray exposures, the improvement comprising: scale dial means having laminagraphic height gradations thereon being operatively connected to said positioning drive means and associated with X-ray film sheets during exposure of the latter so as to mark the area representative of the currently set laminagraphic height on said film sheets; an electromotorized servo-control for adjusting said scale dial means in dependence upon the positioning drive means for the laminagraphic height adjustment.

5. An X-ray examining apparatus as claimed in claim 4, said laminagraphic height gradations on said scale dial means being reproducible through X-rays; and means for supporting the scale dial means and the area representative of the currently set laminagraphic height in adjacency to film-proximte diaphragm means so as to project into the cone of the focused X-rays; said diaphragm means including at least two diaphragm plates; a base plate adjustably supporting said scale dial means, said base plate including a slide member supported on said diaphragm plates for concurrent longitudinal movement along the intersecting location of said two diaphragm plates; said scale dial means comprising a circular scale plate; means for rotatably supporting said scale plate, said scale plate having the laminagraphic gradations on the circumferential edge zones thereof extending above the edges of said diaphragm means defining the X-ray cone and projecting into said X-ray cone.

* * * * *